United States Patent
Jenson et al.

(10) Patent No.: US 9,044,350 B2
(45) Date of Patent: Jun. 2, 2015

(54) ALIGNMENT SHEATH APPARATUS AND METHOD

(75) Inventors: Mark L. Jenson, Greenfield, MN (US); William J. Drasler, Minnetonka, MN (US); Tracee Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2772 days.

(21) Appl. No.: 11/507,103

(22) Filed: Aug. 21, 2006

(65) Prior Publication Data

US 2008/0046066 A1 Feb. 21, 2008

(51) Int. Cl.
| | |
|---|---|
| *A61F 2/954* | (2013.01) |
| *A61F 2/856* | (2013.01) |
| *A61F 2/86* | (2013.01) |
| *A61F 2/852* | (2013.01) |
| *A61F 2/06* | (2013.01) |

(52) U.S. Cl.
CPC .......... *A61F 2/856* (2013.01); *A61F 2/852* (2013.01); *A61F 2/86* (2013.01); *A61F 2/954* (2013.01); *A61F 2002/067* (2013.01); *A61F 2230/0043* (2013.01); *A61F 2250/006* (2013.01); *A61F 2220/005* (2013.01); *A61F 2220/0058* (2013.01); *A61F 2230/001* (2013.01)

(58) Field of Classification Search
CPC ................. A61F 2/954; A61F 2/958
USPC .......... 623/1.11, 1.12, 1.13, 1.15, 1.16, 1.23, 623/1.34, 1.35, 1.37, 903; 606/108, 191, 606/192, 194, 195, 198
See application file for complete search history.

(56) References Cited

U.S. PATENT DOCUMENTS

| | | | |
|---|---|---|---|
| 5,873,906 A | * | 2/1999 | Lau et al. ............ 623/1.12 |
| 6,033,433 A | | 3/2000 | Ehr et al. ................. 623/1 |
| 6,039,749 A | | 3/2000 | Marin et al. .......... 606/198 |

(Continued)

FOREIGN PATENT DOCUMENTS

| | | |
|---|---|---|
| WO | 01/34061 A1 | 5/2001 |
| WO | WO 2004/075792 | 9/2004 |

(Continued)

OTHER PUBLICATIONS

U.S. Appl. No. 11/262,692, filed Oct. 31, 2005, Gregorich et al.

(Continued)

*Primary Examiner* — David Isabella
*Assistant Examiner* — Suba Ganesan
(74) *Attorney, Agent, or Firm* — Vidas, Arrett & Steinkraus

(57) ABSTRACT

The invention is direction to an alignment apparatus comprising a central sheath, an alignment sheath, and at least one stent. The central sheath and the alignment sheath each have a wall and a distal end where the wall of the alignment sheath is engaged to the wall of the central sheath. The wall of the central sheath defines a central lumen that has a central guide wire extending therethrough and the wall of the alignment sheath defines an alignment lumen that has an alignment guide wire extending therethrough. The distal end of the alignment sheath is positioned proximally to the distal end of the central sheath. The alignment apparatus has at least one stent disposed about one of the alignment guide wire or the central guide wire. The at least one stent has a pre-delivered state so that when the at least one stent is in the pre-delivered state, it is contained within at least one of the central sheath and the alignment sheath.

19 Claims, 15 Drawing Sheets

(56) References Cited

U.S. PATENT DOCUMENTS

| | | | |
|---|---|---|---|
| 6,096,073 A | 8/2000 | Webster et al. | |
| 6,143,002 A | 11/2000 | Vietmeier | |
| 6,251,133 B1 * | 6/2001 | Richter et al. | 623/1.16 |
| 6,261,319 B1 | 7/2001 | Kveen et al. | 623/1.15 |
| 6,482,211 B1 | 11/2002 | Choi | 606/108 |
| 6,508,836 B2 | 1/2003 | Wilson et al. | 623/1.35 |
| 6,520,988 B1 * | 2/2003 | Colombo et al. | 623/1.35 |
| 6,579,312 B2 | 6/2003 | Wilson et al. | 623/1.35 |
| 6,596,020 B2 | 7/2003 | Vardi et al. | 623/1.11 |
| 6,692,483 B2 | 2/2004 | Vardi et al. | 604/529 |
| 6,746,411 B2 | 6/2004 | Khaw | 600/585 |
| 6,908,477 B2 * | 6/2005 | McGuckin et al. | 623/1.11 |
| 6,962,602 B2 | 11/2005 | Vardi et al. | 623/1.11 |
| 7,695,508 B2 * | 4/2010 | Der Leest et al. | 623/1.35 |
| 2001/0003161 A1 | 6/2001 | Vardi et al. | |
| 2001/0025195 A1 * | 9/2001 | Shaolian et al. | 623/1.35 |
| 2002/0193873 A1 | 12/2002 | Brucker et al. | 623/1.35 |
| 2003/0028233 A1 * | 2/2003 | Vardi et al. | 623/1.11 |
| 2004/0172119 A1 | 9/2004 | Eidenschink | 623/1.11 |
| 2004/0172121 A1 | 9/2004 | Eidenschink et al. | 623/1.11 |
| 2005/0038494 A1 | 2/2005 | Eidenschink | 623/1.11 |
| 2005/0149161 A1 | 7/2005 | Eidenschink et al. | 623/1.11 |
| 2005/0154442 A1 | 7/2005 | Eidenschink et al. | 623/1.11 |
| 2005/0182473 A1 | 8/2005 | Eidenschink et al. | 623/1.11 |
| 2005/0273149 A1 | 12/2005 | Tran et al. | 623/1.11 |
| 2006/0074475 A1 | 4/2006 | Gumm | 623/1.11 |
| 2006/0074476 A1 | 4/2006 | Holman et al. | |

FOREIGN PATENT DOCUMENTS

| | | |
|---|---|---|
| WO | WO 2005/096995 | 10/2005 |
| WO | WO 2006/085304 | 8/2006 |

OTHER PUBLICATIONS

U.S. Appl. No. 11/273,186, filed Nov. 14, 2005, Eidenschink et al.
U.S. Appl. No. 11/314,115, filed Dec. 20, 2005, Sorenson et al.
U.S. Appl. No. 11/368,964, filed Mar. 6, 2006, Meyer et al.

* cited by examiner

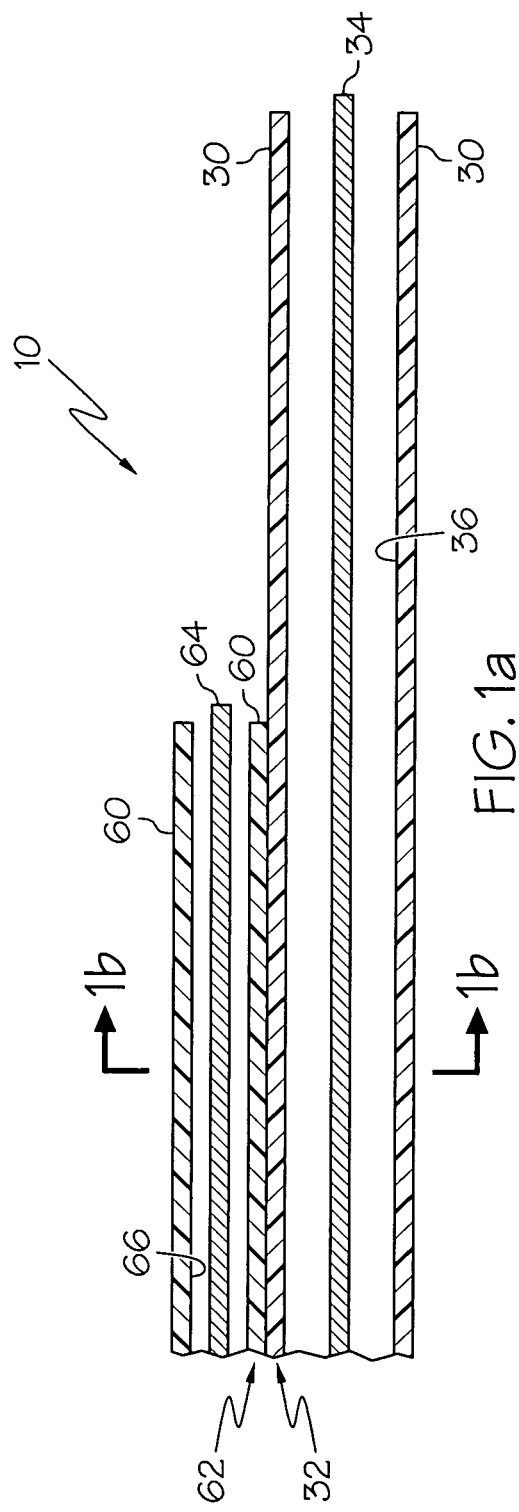
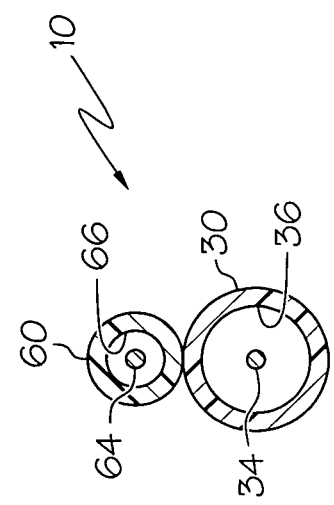
FIG. 1a
FIG. 1b

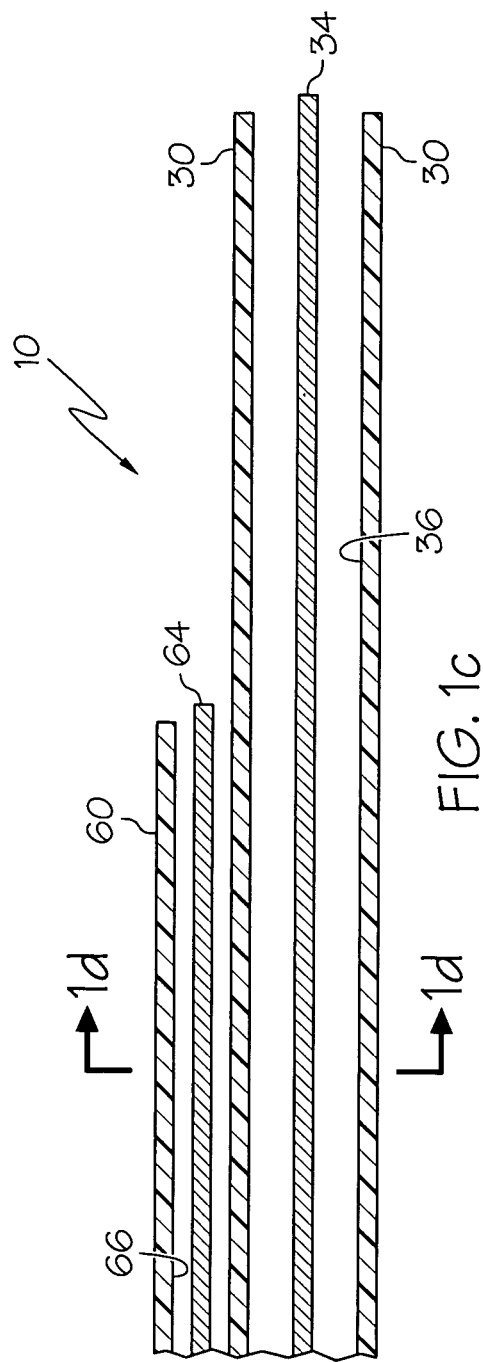
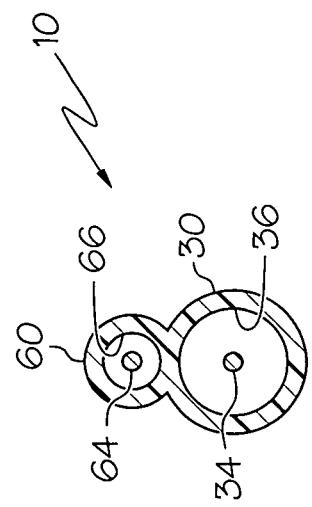

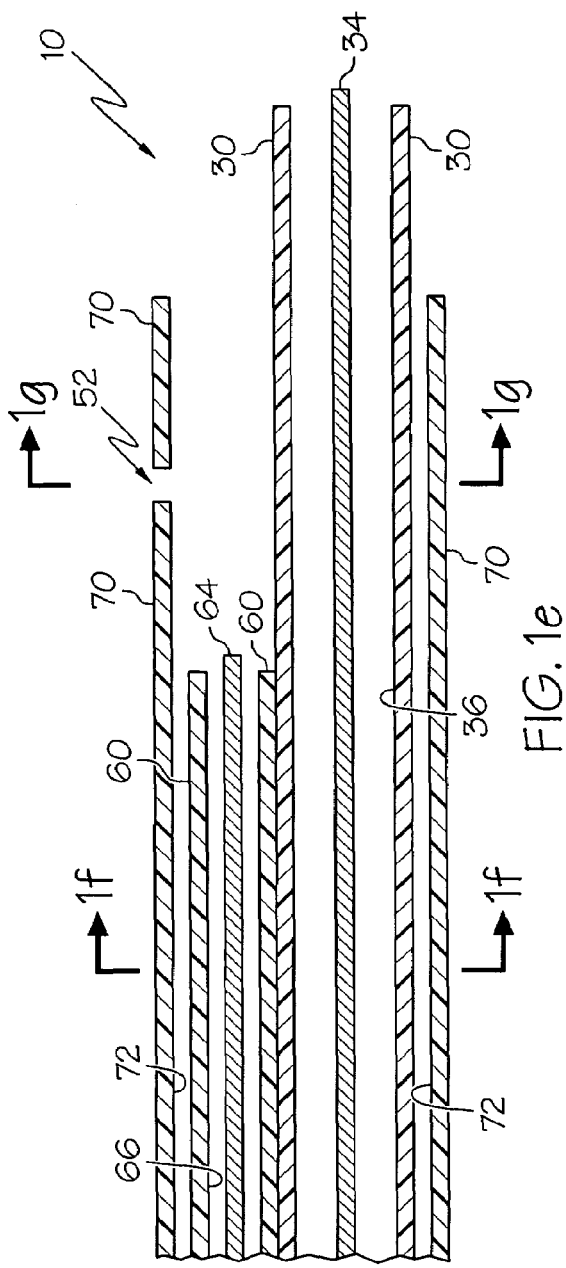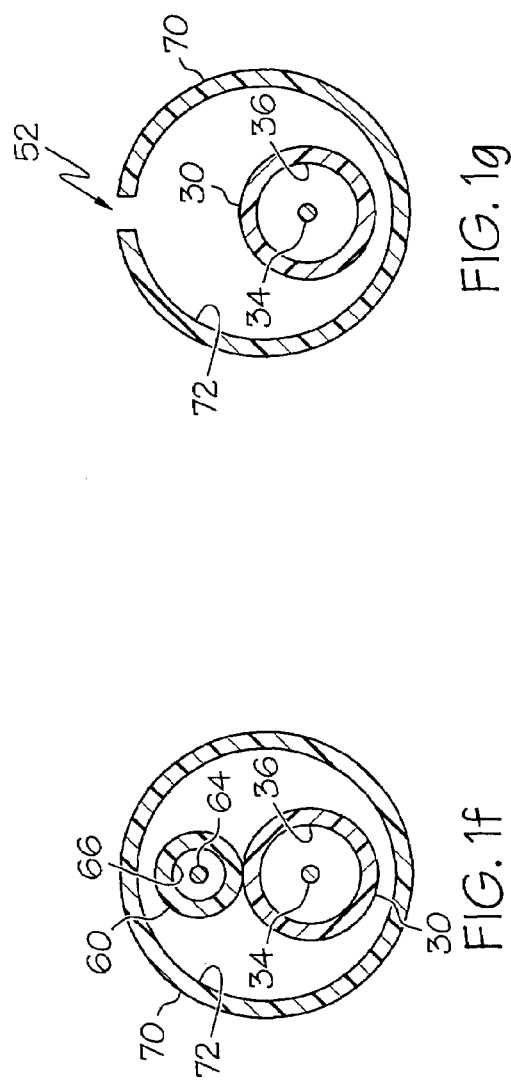
FIG. 1e
FIG. 1f
FIG. 1g

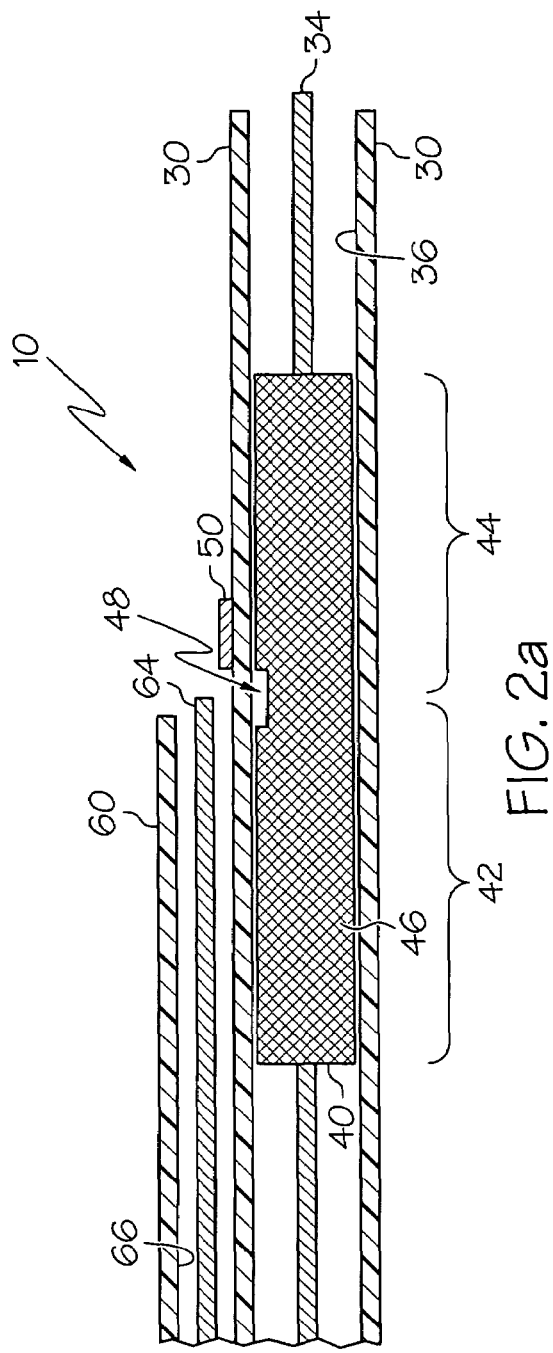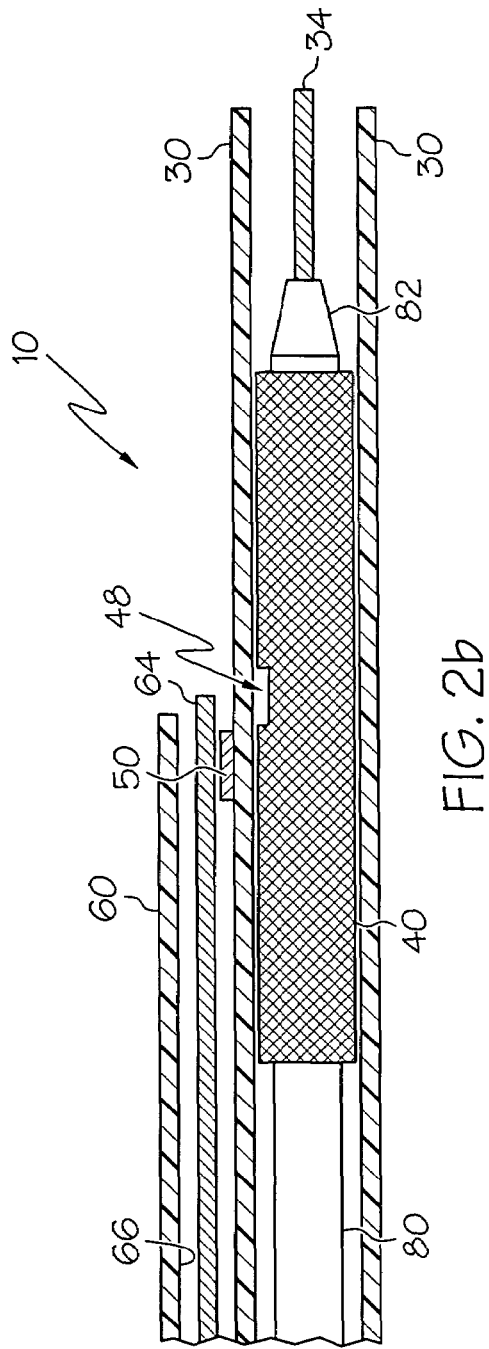

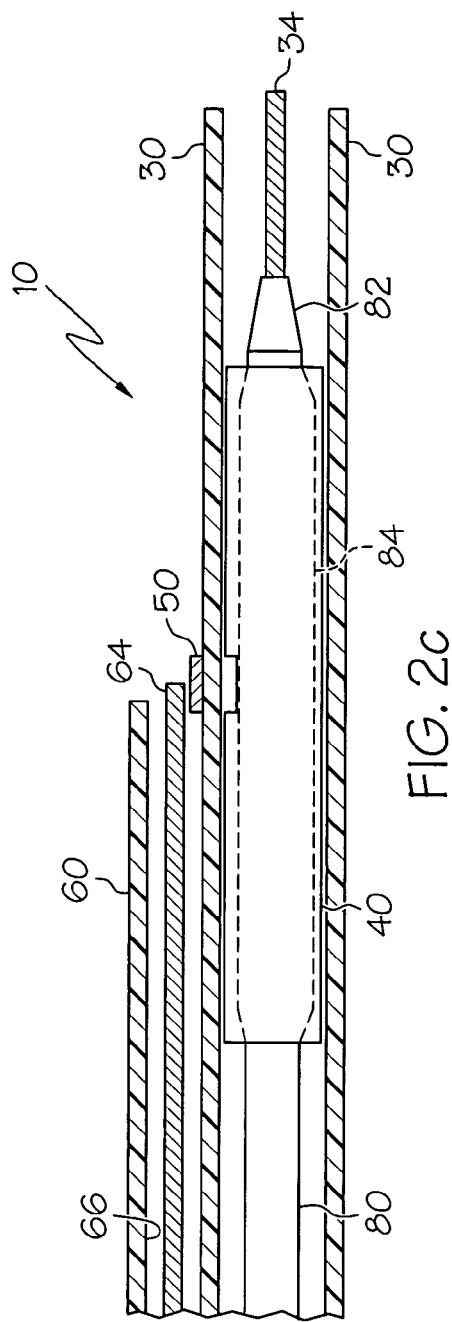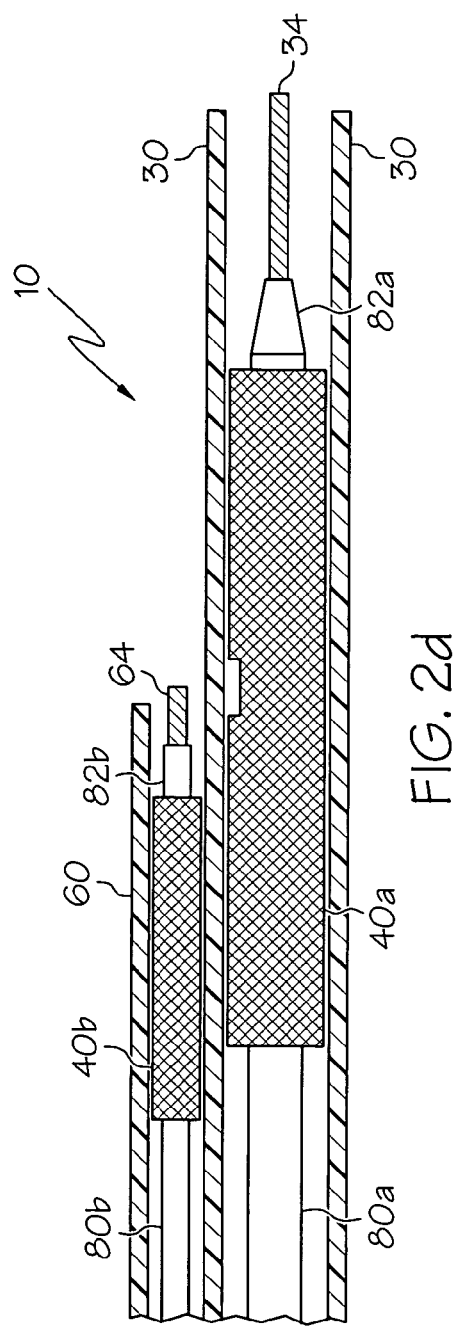

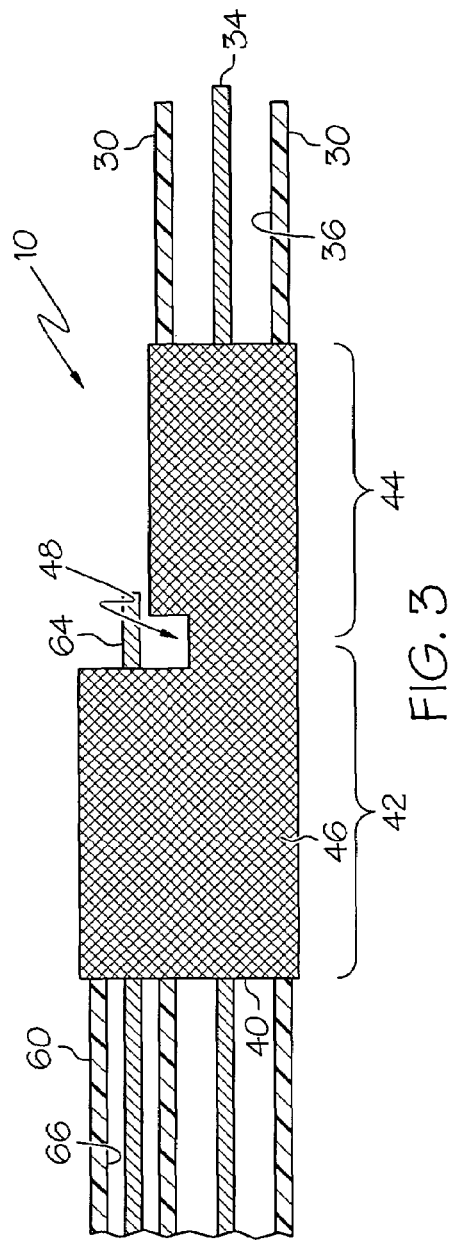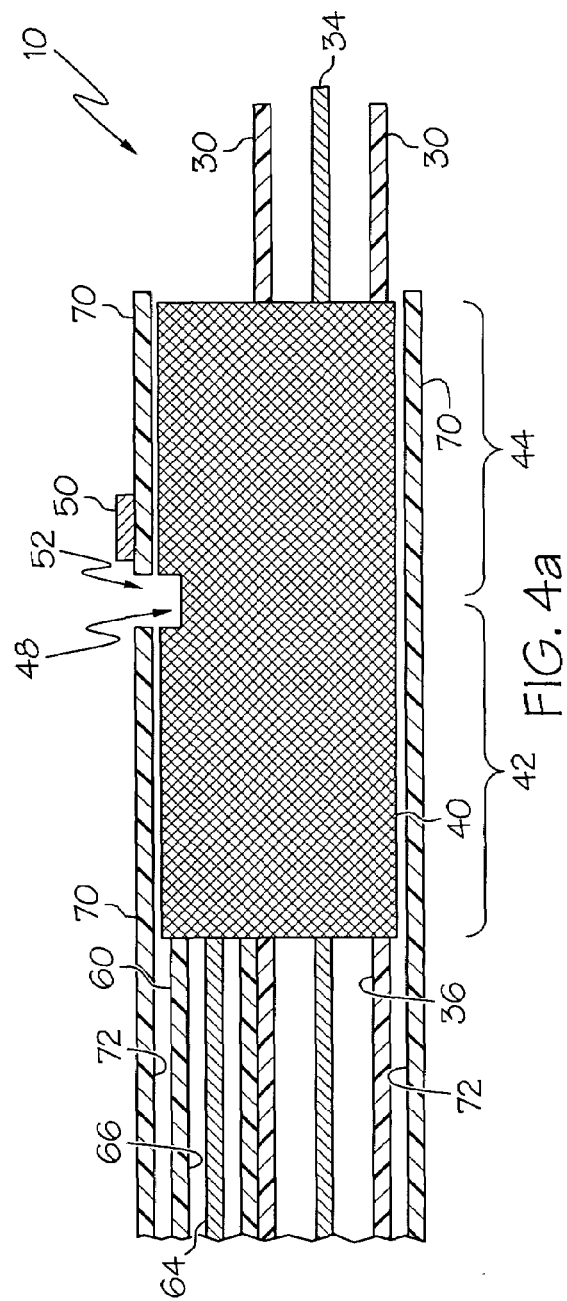

ALIGNMENT SHEATH APPARATUS AND METHOD

CROSS-REFERENCE TO RELATED APPLICATIONS

Not Applicable

STATEMENT REGARDING FEDERALLY SPONSORED RESEARCH

Not Applicable

FIELD OF THE INVENTION

The present invention relates generally to intravascular devices for performing medical procedures.

BACKGROUND OF THE INVENTION

Intravascular catheters are currently utilized in a wide variety of minimally-invasive or percutaneous medical procedures. Generally, an intravascular catheter enables a physician to remotely perform a medical procedure by inserting the catheter into the vascular system of the patient at an easily accessible location and navigating the tip of the catheter to a desirable target site. By this method, virtually any target site in the patient's vascular system may be remotely accessed.

Typically, a percutaneous procedure begins with the step of inserting a distal portion of the catheter into the patient's vasculature at a convenient location. Once the distal portion of the catheter has entered the patient's vascular system the physician may urge the distal tip forward by applying forces to the proximal portion of the catheter. Typically, the path taken by a catheter through the vascular system is tortuous, requiring the catheter to change direction frequently. While advancing the catheter through the tortuous path of the patient's vasculature, the physician must steer the distal end of the catheter. During a percutaneous procedure, the physician typically is not able to manipulate the distal portion of the catheter directly. For this reason, physicians typically must steer the distal end of the catheter by applying torsional forces to the proximal portion of the catheter.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

Delivery systems that are used to advance a stent to a bifurcation need to be steered rotationally so that the stent is properly aligned in relation to the branch vessel so that blood flows through the stent in the main vessel into the branch vessel. Stent delivery systems used to position stents at or near a bifurcation are shown and described in U.S. patent application Ser. No. 10/375,689, filed Feb. 27, 2003, entitled Rotating Balloon Expandable Sheath Bifurcation Delivery; U.S. patent application Ser. No. 10/657,472, filed Sep. 8, 2003, entitled Rotating Balloon Expandable Sheath Bifurcation Delivery; U.S. patent application Ser. No. 10/747,546, filed Dec. 29, 2003, entitled Edge Protection and Bifurcated Stent Delivery System; and U.S. patent application Ser. No. 10/757,646, filed Jan. 13, 2004, entitled Bifurcated Stent Delivery System, the entire content of each of the above U.S. Patent Applications are incorporated herein by reference in their entirety.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In order to maintain place a stent at a bifurcation with the proper orientation, embodiments of the present invention are directed to an alignment apparatus and stents designed to be used with the alignment apparatus.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

FIG. 1a is a cross-sectional side view of the distal end region of an embodiment of the alignment apparatus.

FIG. 1b is a cross-section of the alignment apparatus of FIG. 1a taken at line 1b-1b.

FIG. 1c is a cross-sectional side view of the distal end region of a second embodiment of the alignment apparatus.

FIG. 1d is a cross-section of the alignment apparatus of FIG. 1c taken at line 1d-1d.

FIG. 1e is the alignment apparatus of FIG. 1a with an exterior sheath.

FIG. 1f is a cross-section of the alignment apparatus of FIG. 1e taken at line 1f-1f.

FIG. 1g is a cross-section of the alignment apparatus of FIG. 1e taken at line 1g-1g.

FIG. 2a is the alignment apparatus of FIG. 1c with a stent.

FIG. 2b is the alignment apparatus of FIG. 1c with a stent engaged to a catheter positioned within the central sheath of the alignment apparatus.

FIG. 2c is the alignment apparatus of FIG. 1c with a stent engaged to a balloon catheter positioned within the central sheath of the alignment apparatus.

FIG. 2d is the alignment apparatus of FIG. 2b with a second stent engaged to a catheter positioned within the alignment sheath of the alignment apparatus.

FIG. 3 is the alignment apparatus of FIG. 1c with an alternative stent configuration.

FIG. 4a is the alignment apparatus of FIG. 1e with a stent.

FIG. 7c is a flat view of a stent with a slit where the side branch has a different geometry than the side branch geometry of the stent in FIG. 7a.

DETAILED DESCRIPTION OF THE INVENTION

Figure 4B:
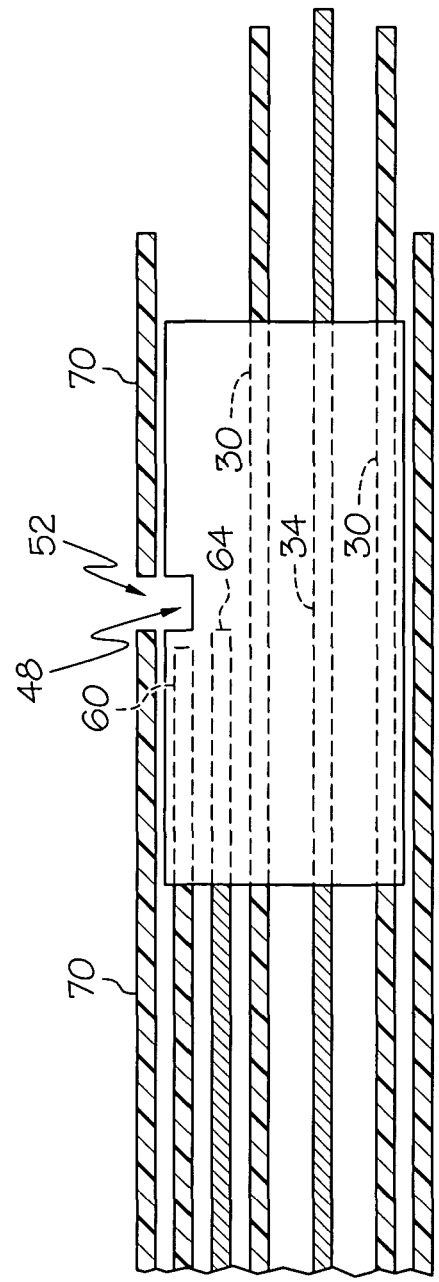
FIG. 4b is the alignment apparatus in FIG. 4a showing the placement of the alignment guide wire within the stent.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 5A:
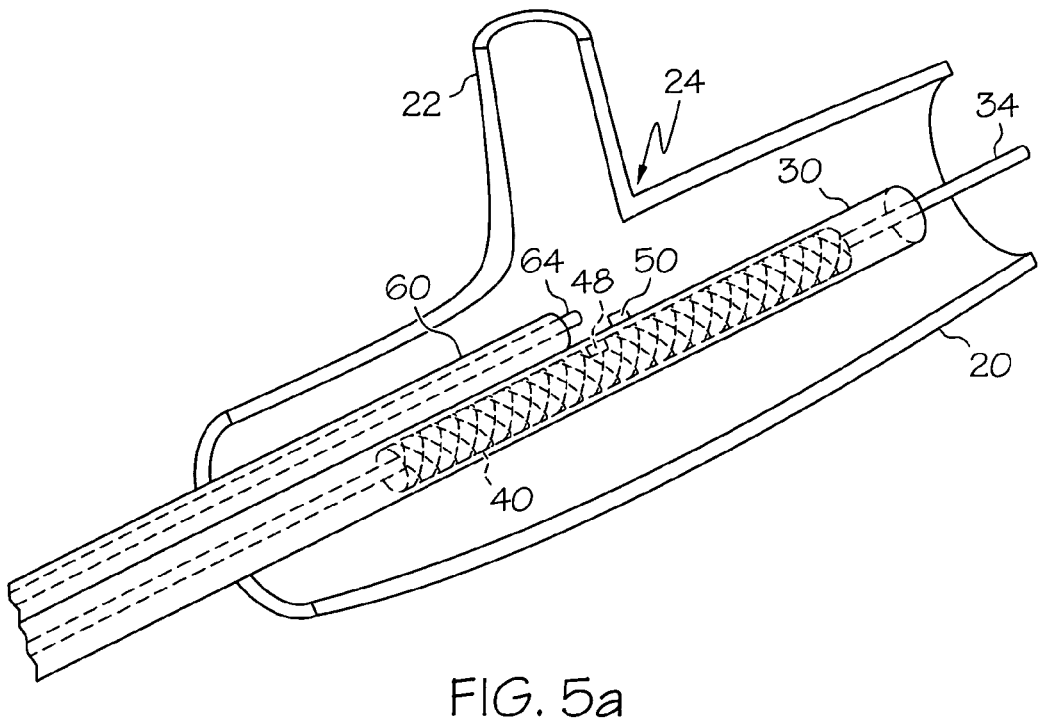
FIG. 5a is a view of alignment apparatus of FIG. 2a at the point of a bifurcation within the vasculature.

FIGS. 1a, 1c and 1e illustrate different embodiments of the inventive alignment apparatus 10. Alignment apparatus 10 is configured to aid in the advancement and alignment of a stent 40 at a vessel bifurcation such as is shown in FIG. 5a for example.

In the various embodiments shown and described herein the alignment apparatus 10 comprise a central sheath 30 which defines a central lumen 36 for passage of a central guide wire 34 therethrough. The alignment apparatus 10 also comprises an alignment sheath 60 that defines an alignment lumen 66 for passage of an alignment guide wire 64 therethrough. The distal end of the alignment sheath 60 is proximal to the distal end of the central sheath 30.

In the embodiment illustrated in FIG. 1a, the wall 32 of the central sheath 30 does not form a portion of the wall 62 of the alignment sheath 60. This can be seen in FIG. 1b, which is a cross-section of the alignment apparatus 10 in FIG. 1a. In one embodiment the entire length of the alignment sheath is engaged to the central sheath. In one embodiment, only the distal end region of the alignment sheath 60 is engaged to the central sheath 30. Engagement between the alignment sheath 60 and the central sheath 30 may be by bonding, welding, adhering adhesively, engaging, mechanically engaging, or otherwise connecting the surfaces of the wall 62 of the alignment sheath 60 with the wall 32 of the central sheath 30.

In contrast to the first embodiment of the alignment apparatus 10, in the embodiment shown in FIG. 1c, the wall 32 of the central sheath 30 forms a portion of the wall 62 of the central sheath 30, i.e. the central sheath 30 and the alignment sheath 60 have a wall 62 in common. This "shared" wall is illustrated in FIG. 1 d which is a cross-section of the alignment apparatus 10 in FIG. 1c.

FIG. 1e illustrates a third embodiment of the alignment apparatus 10. In this embodiment, the alignment apparatus 10 has an external sheath 70 that extends distally from the distal end of the alignment sheath 60 and alignment guide wire 64. The external sheath 70 has at least one hole 52. When the hole 52 is positioned distal from the distal end of the alignment sheath 60, the alignment guide wire 64 can pass through the hole 52 into a branch vessel, as is discussed in further detail herein. Thus, the hole 52 is large enough to accommodate the passage of the alignment guide wire 64 therethrough.

Although not shown, the embodiment of FIG. 1c can also have an external sheath 70. The space between the external sheath 70 and the alignment sheath 60 is an external sheath lumen 72. FIGS. 1f and 1g show cross-sections of the alignment apparatus 10 illustrated in FIG. 1e. In at least one embodiment, the external sheath 70 rotates about the alignment sheath 60 and the central sheath 30.

The alignment apparatus embodiments depicted in FIGS. 1a, 1c and 1e can be used to deliver a stent 40 to a bifurcation within the body. FIGS. 2a-c, 3 and 4 illustrate the different ways a stent 40 can be delivered by the different embodiments of the alignment apparatus 10. FIG. 2a illustrates the alignment apparatus 10 of FIG. 1c with a stent 40 positioned and contained within the central sheath 30 of the alignment apparatus 10.

Figure 7A:
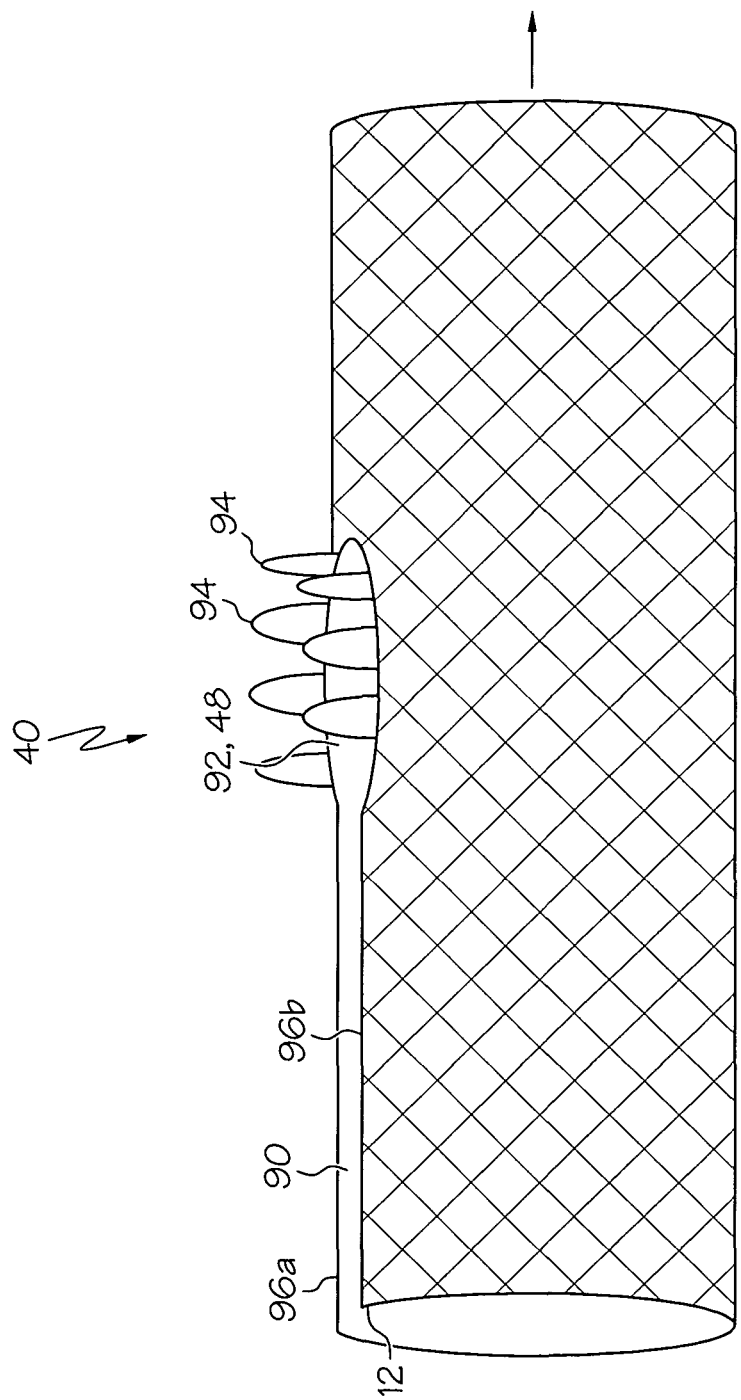
FIG. 7a is a side view of a stent for a bifurcation in an expanded state where the stent has a slit and a side branch with petals.
Figure 7B:
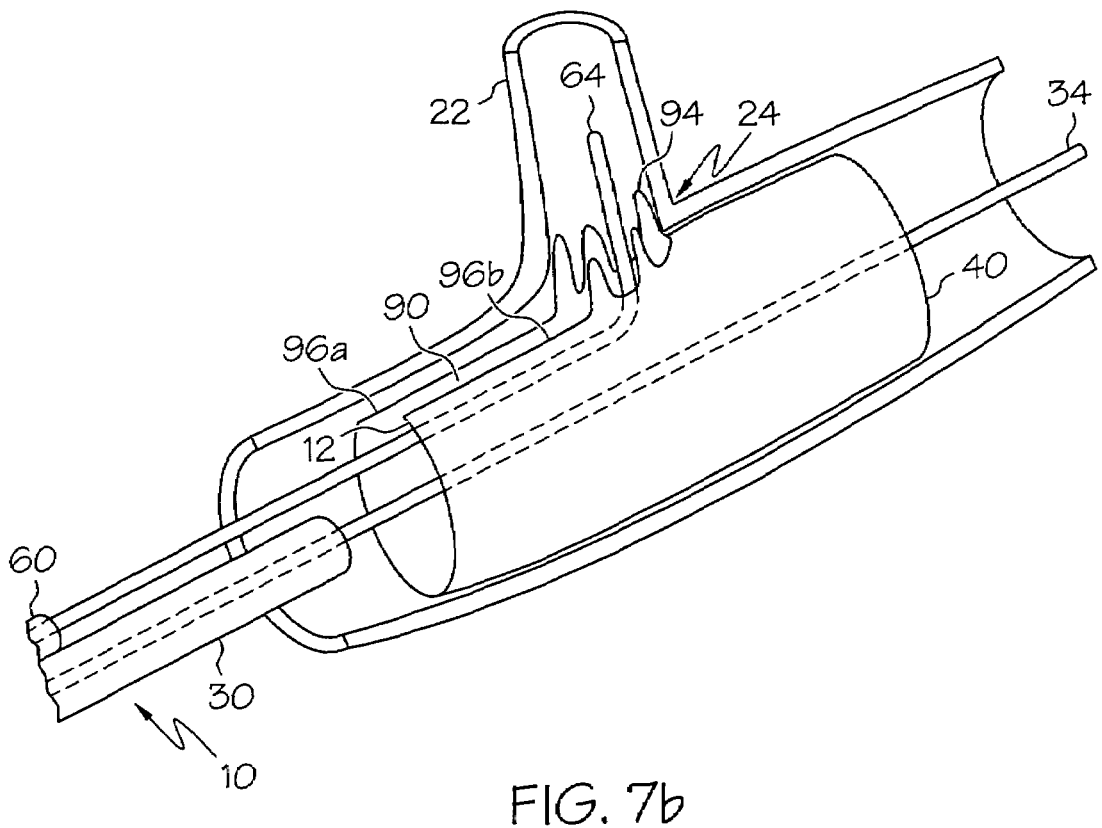
FIG. 7b is a view of the stent of FIG. 7a deployed within a vessel after the sheaths have been withdrawn from the stent.
Figure 7C:
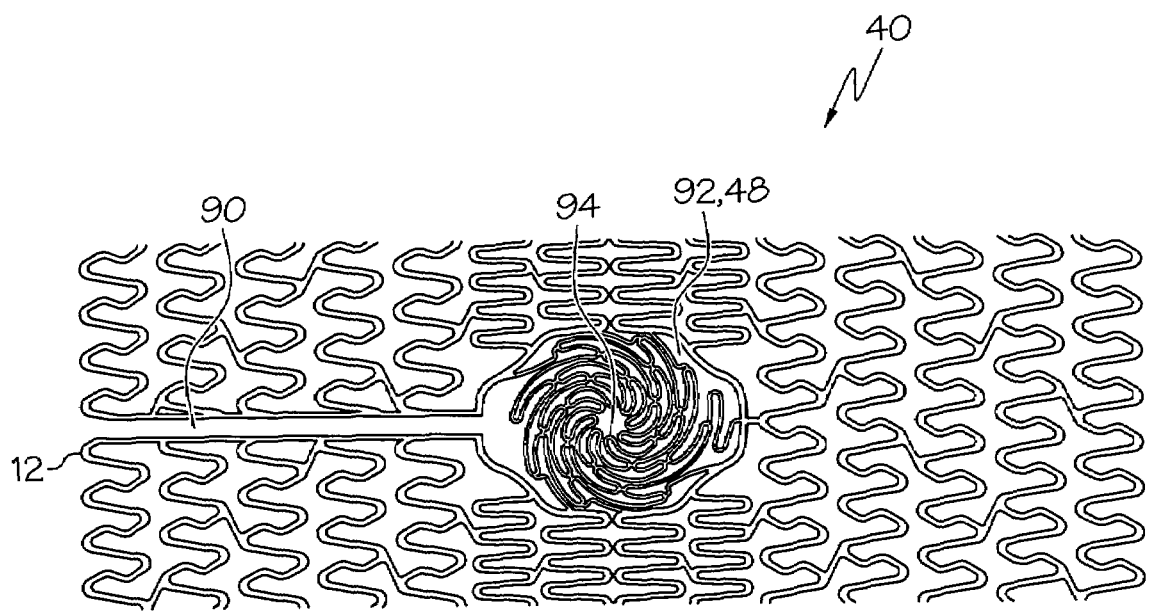
Figure 8A:
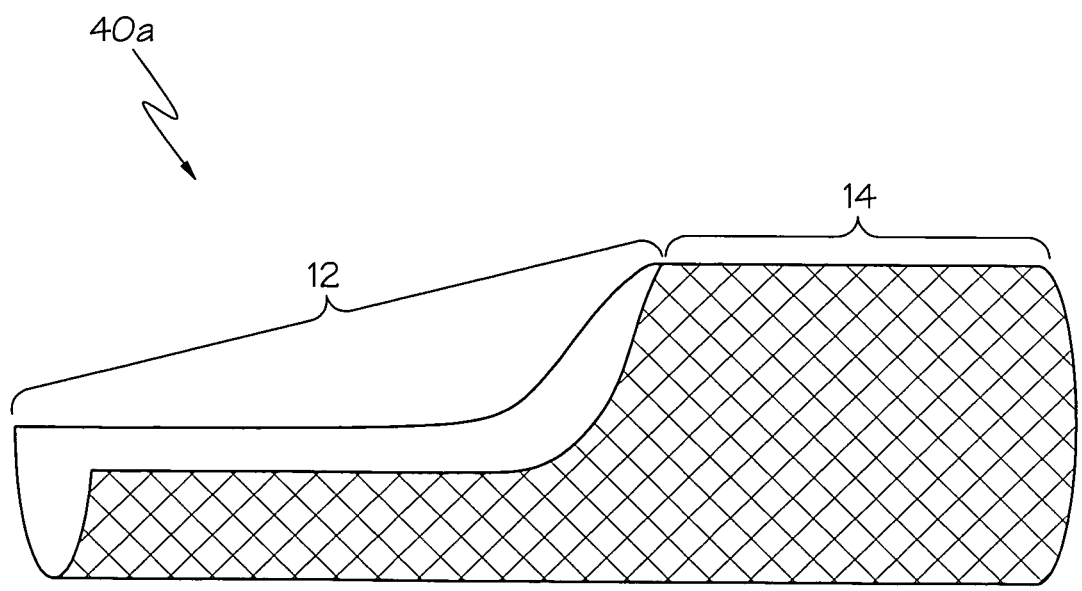
FIG. 8a is a side view of a first stent of a dual stent for a bifurcation.
Figure 8B:
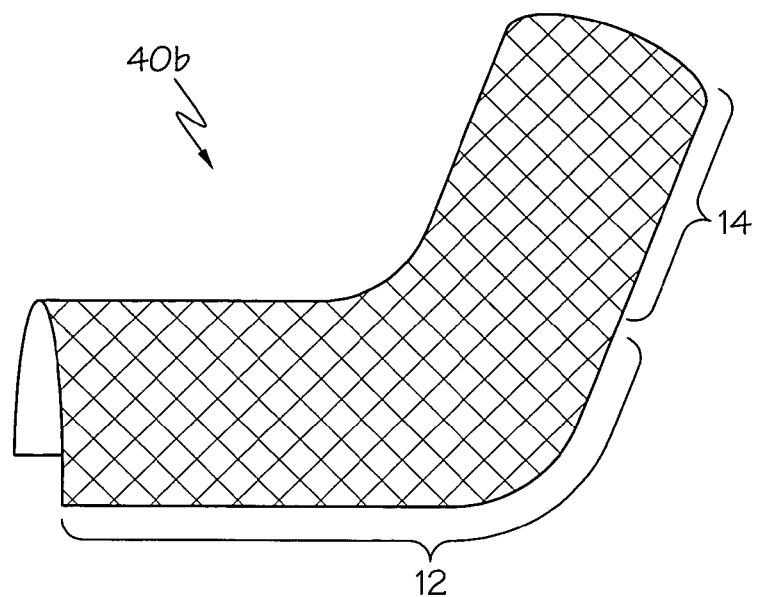
FIG. 8b is a side view of a second stent of a dual stent for a bifurcation.
Figure 8C:
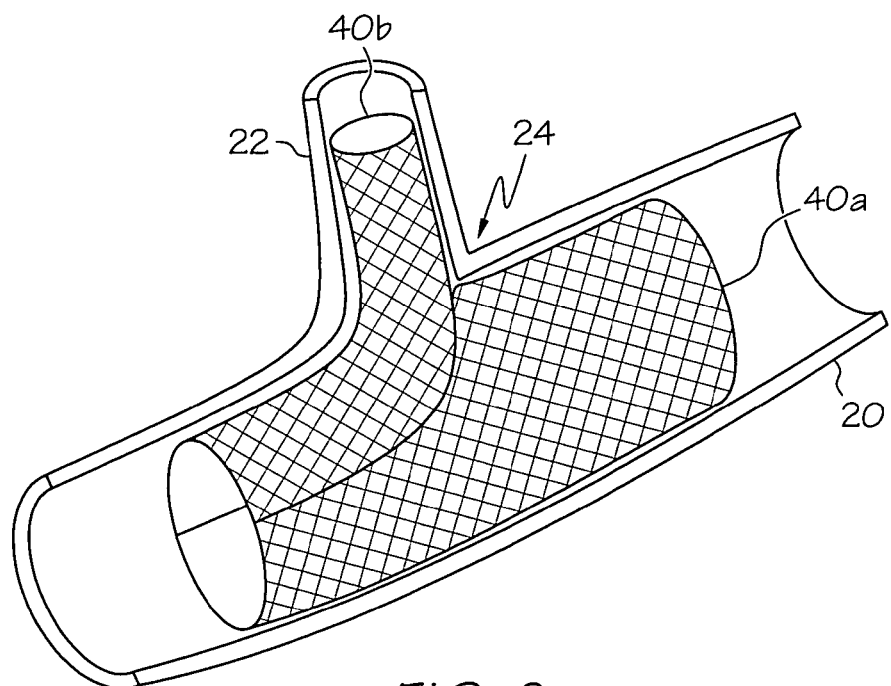
FIG. 8c is a side view of the dual stent of FIG. 8a at a bifurcation within a vessel.

Since the plurality of struts 46 that form the substantially tubular body of the stent 40 can form any pattern, the strut pattern of the stents 40 in most of the figures of this application is indicated by crossed lines. In at least one embodiment, the tubular body of the stent 40 has a slit opening, as illustrated in FIGS. 7a-c and discussed in further detail below. In at least one embodiment, a dual stent 40 is used at the bifurcation, as illustrated in FIGS. 8a-8c and discussed in further detail below.

In addition, the stent 40 in the majority of the figures is shown as having a noticeable side hole 48. The size of the side hole 48 is emphasized in these figures in order to facilitate the understanding of the inventive alignment apparatus 10. In at least one embodiment, side hole 48 is a cell like the other cells formed by the plurality of struts 46. Thus the size of the side hole 48 when compared to the other cells of the stent 40 may be a larger size, a smaller size or the same size as the other cells. In at least one embodiment, the side hole 48 is larger than the other cells of the stent 40. In at least one embodiment the side hole 48 has projections that extend into the secondary branch vessel, much like those shown and described in U.S. patent application Ser. No. 11/273,186, filed Nov. 14, 2005, entitled Stent with Spiral Side-Branch Support Designs and U.S. patent application Ser. No. 11/368964, filed Mar. 6, 2006, entitled Bifurcation Stent with Uniform Side Branch Projection. The stent 40 may also have a plurality of side holes, as shown and described in U.S. patent application Ser. No. 11/314,115, filed Dec. 20, 2005, entitled Bifurcated Stent with Multiple Locations for Side Branch Access. Since the side hole 48 may be the same size as the other cells of the stent 40, the pattern formed by the plurality of struts 46 can be a uniform pattern, much like those shown and described in U.S. patent application Ser. No. 11/262,692, filed Oct. 31, 2005, entitled Stent Configurations; U.S. Pat. No. 6,261,319, entitled An Improved Stent and U.S. Pat. No. 6,033,433, entitled Improved Stent Configurations. Any of the cells of a uniform patterned stent 40 may be utilized as a side hole 48 within the meaning of this application. The entire content of all the above mentioned patent applications and patents are incorporated herein by reference.

Returning to the figures, FIG. 2b illustrates the alignment apparatus of FIG. 1c with a stent 40 engaged to a catheter 80 which is positioned within the central sheath 30. In FIG. 2c, the catheter 80 has a balloon 84 to which the stent 40 is engaged. In FIG. 2d, the alignment apparatus 10 of FIG. 2b has a second stent 40 engaged to a catheter positioned within the alignment sheath 60. A catheter, with or without a balloon, may be part of any of the alignment apparatus embodiments described herein. The stent 40 may be engaged to the catheter 80 by friction, interference, tack, fiber, or other means known by those skilled in the art. In at least one embodiment, engaging the stent 40 to a catheter 80 maintains the stent 40 in the proper orientation while the central sheath 30 and the alignment sheath 60 are withdrawn. Then the stent 40 can be expanded and deployed. If the stent 40 is self-expanding, it will deploy without assistance, as is known in the art. If the stent 40 is balloon expandable, then, using the embodiment illustrated in FIG. 2c., once the central sheath 30 and the alignment sheath 60 have been withdrawn, the balloon 84 would be inflated to expand and deploy the stent 40 into the body lumen. In one embodiment, the central guide wire 34 temporarily engages the stent 40 while the central sheath 30 and the alignment sheath 60 are withdrawn and then disengages to allow the stent 40 to deploy into the body lumen.

FIGS. 3 and 4a and 4b show the alignment apparatus 10 of FIG. 1e with different stent 40 conformations. In FIG. 3, the entire circumference of the proximal portion 42 of the stent 40 is engaged to the alignment sheath 60 and the entire circumference of the distal portion 44 of the stent 40 is engaged to the central sheath 30. Thus, the stent 40 is fully engaged to both the alignment sheath 60 and the central sheath 30. In one embodiment, an external sheath 70 is disposed about the stent which is engaged to both the alignment sheath and the central sheath. In one embodiment, the external sheath 70 can rotate about the stent which is engaged to both the alignment sheath and the central sheath.

The alignment apparatus 10 of FIG. 4a is designed to be utilized with a self expanding stent 40. The exterior sheath 70 maintains the stent 40 in an unexpanded state until the exterior sheath 70 is withdrawn away from the stent 40. In FIG. 4a, the entire circumference of the proximal portion 42 of the stent 40 is engaged to the alignment sheath 60 while only a portion of circumference of the distal portion 44 of the stent 40 is engaged to the central sheath 30. Thus, the proximal portion 42 of the stent 40 is fully engaged to the alignment apparatus 10 while the distal portion 44 of the stent 40 is partially engaged to the alignment apparatus 10. This can be seen in FIG. 4b which shows the positions of the sheath walls and the guide wires 34, 64 within the stent 40. In one embodiment, the external sheath 70 rotates about the stent 40 which is engaged to both the alignment sheath 60 and the central sheath 30.

The embodiments of the alignment apparatuses 10 described above may be used to position at least one stent 40 at, or near, a bifurcation. FIGS. 5a-5d illustrate how the alignment apparatus 10 embodiment of FIG. 1c can be used to place a stent 40 at a bifurcation, but these steps are applicable to all the embodiments unless a difference for a particular embodiment is specifically noted. In FIG. 5a, the alignment apparatus 10 has been advanced through the vasculature by means of the central guide wire 34. The position of the alignment apparatus 10 in relation to the bifurcation can be visualized by means of a marker 50 which is on the central sheath 30.

In at least one embodiment, the alignment apparatus 10 has at least one marker 50, as shown in FIGS. 2a-2c and 5a-d. The marker 50 is an area, band, coating, member, etc. that is detectable by imaging modalities such as X-ray, MRI, ultrasound, etc. In FIGS. 2a-2c the marker 50 is positioned about the side hole 48 of the stent 40. In at least one embodiment, the stent 40 has a marker 50 positioned near the side hole 48. In at least one embodiment, the marker 50 is distal to the side hole 48. In at least one embodiment, at least a portion of the stent and/or adjacent alignment apparatus is at least partially radiopaque. Once the marker 50 is in the proper longitudinal position within the main vessel 20, the alignment apparatus 10 can be rotated so that the marker 50 is positioned next to the ostium of the branch vessel 22. In at least one embodiment, advancing the alignment guide wire 64 into the branch vessel 22 causes only the distal end of the alignment apparatus 10 to be rotated, instead of the entire length of the apparatus, thereby causing less strain on the vasculature.

Figure 5B:
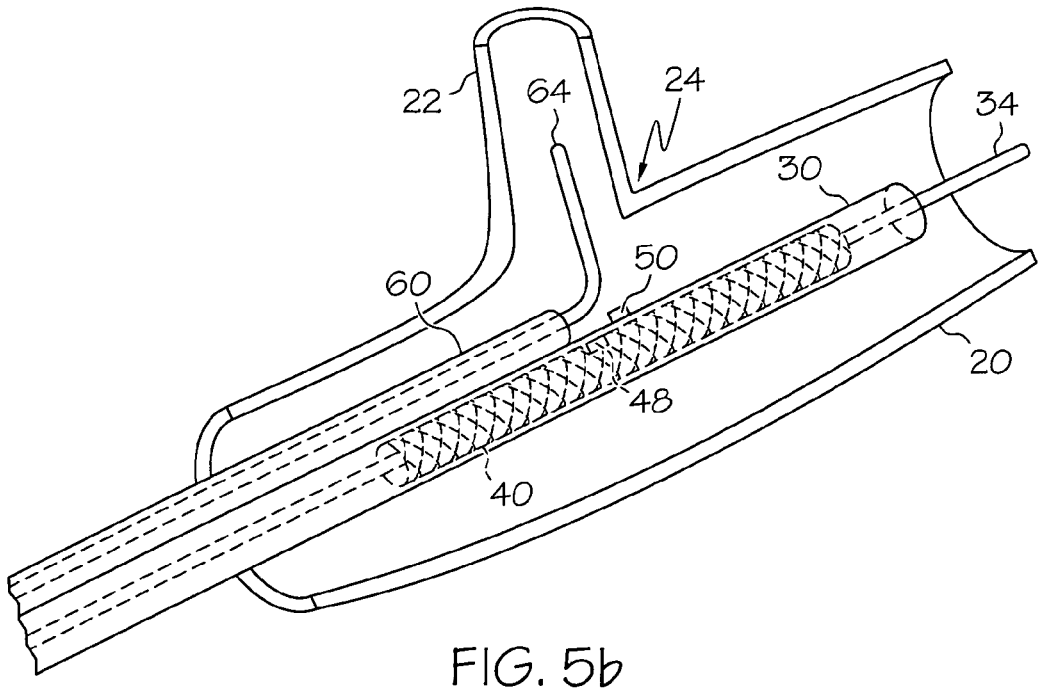
FIG. 5b is a view of the alignment apparatus of FIG. 5a after the alignment guide wire has been advanced into the branch vessel.

Once the alignment apparatus 10 is in the proper longitudinal and axial position within the main vessel 20, the alignment guide wire 64 is advanced into the branch vessel 22, as shown in FIG. 5b. In at least one embodiment, advancing the alignment guide wire 64 into the branch vessel 22 maintains the alignment apparatus 10 in the proper orientation within the main vessel 20 at the site of the bifurcation 24 while the stent 40 is being deployed. Note that embodiments of the alignment apparatus 10 where the stent 40 is positioned within the central sheath 30, the alignment guide wire 64 does not need to pass through the stent 40 or through the side hole 48 of the stent 40 in order to orient the alignment apparatus 10 to the branch vessel 22.

Figure 5C:
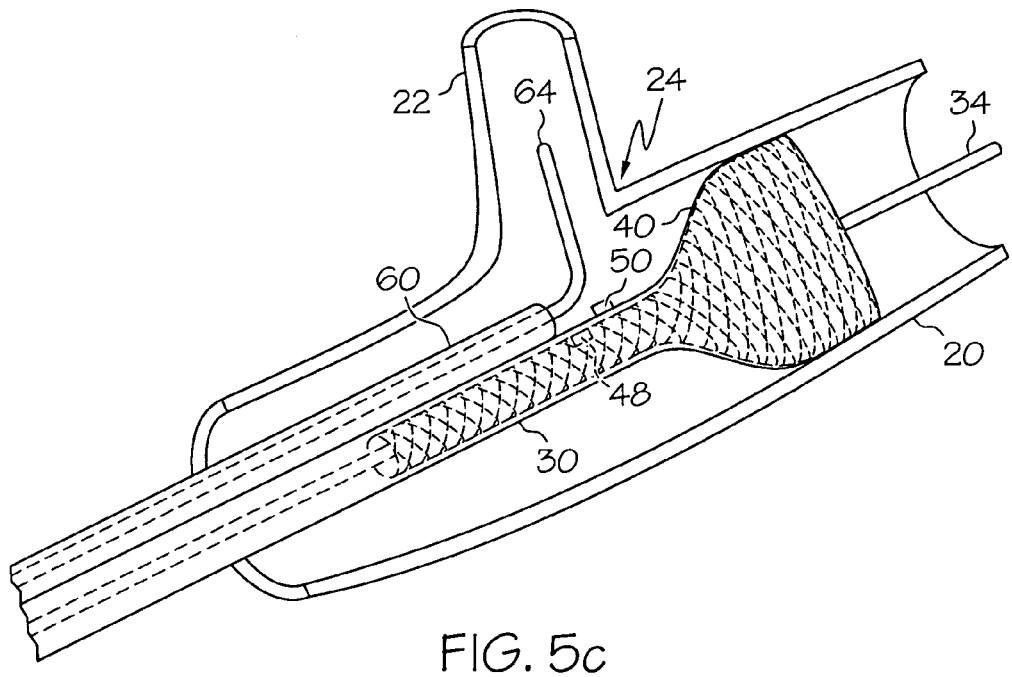
FIG. 5c is view of the distal end region of the stent within the central sheath expanding after the alignment apparatus has been partially withdrawn away from the stent.
Figure 5D:
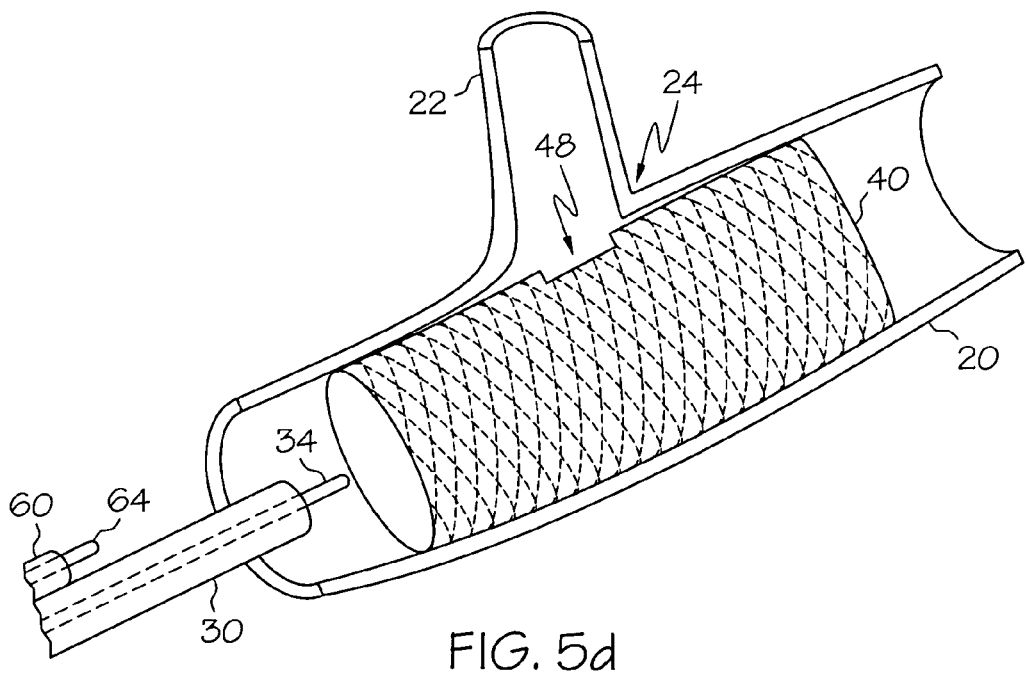
FIG. 5d is a view of the deployed stent after the alignment apparatus has been withdrawn away from the stent.

To deploy a self-expanding stent 40, the alignment apparatus 10 can be withdrawn proximally so that the central sheath 30 no longer surrounds the distal end region of the stent 40, as shown in FIG. 5c. Because the distal end region of the self-expanding stent 40 is not constrained by the central sheath 30, the distal end region deploys into the main vessel 20. Once the stent 40 is partially deployed, the alignment apparatus 10 can be withdrawn further to expose the rest of the stent 40 without the altering the desired orientation of the stent 40. FIG. 5d shows the stent 40 fully deployed within the main vessel 20 with the alignment apparatus 10 being withdrawn.

If the stent 40 deployed at the bifurcation does not have a side hole 48 that is larger than the other cells of the stent 40, e.g. if all the cells of the stent 40 have an equal size, it will be necessary to create a side hole 48 where the stent 40 crosses the ostium of the branch vessel 22 to facilitate blood flow from the main vessel 20 to the branch vessel 20 or vice-versa. This can be done by spreading apart the struts 46 forming a cell positioned in the center of the ostium with a balloon or by other means known in the art.

Figure 7D:
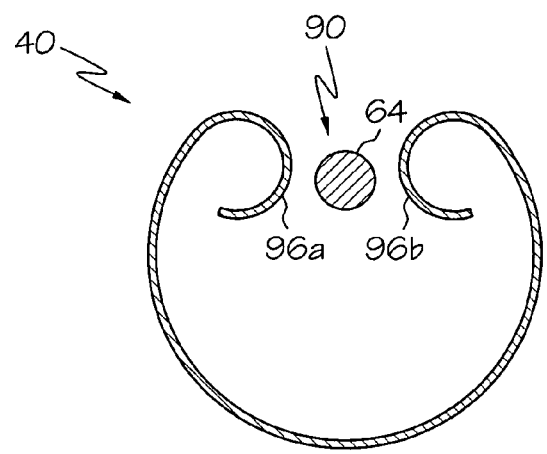
FIG. 7d is an end view of the stent of FIG. 7a with a slit region with rolled edges.
Figure 7E:
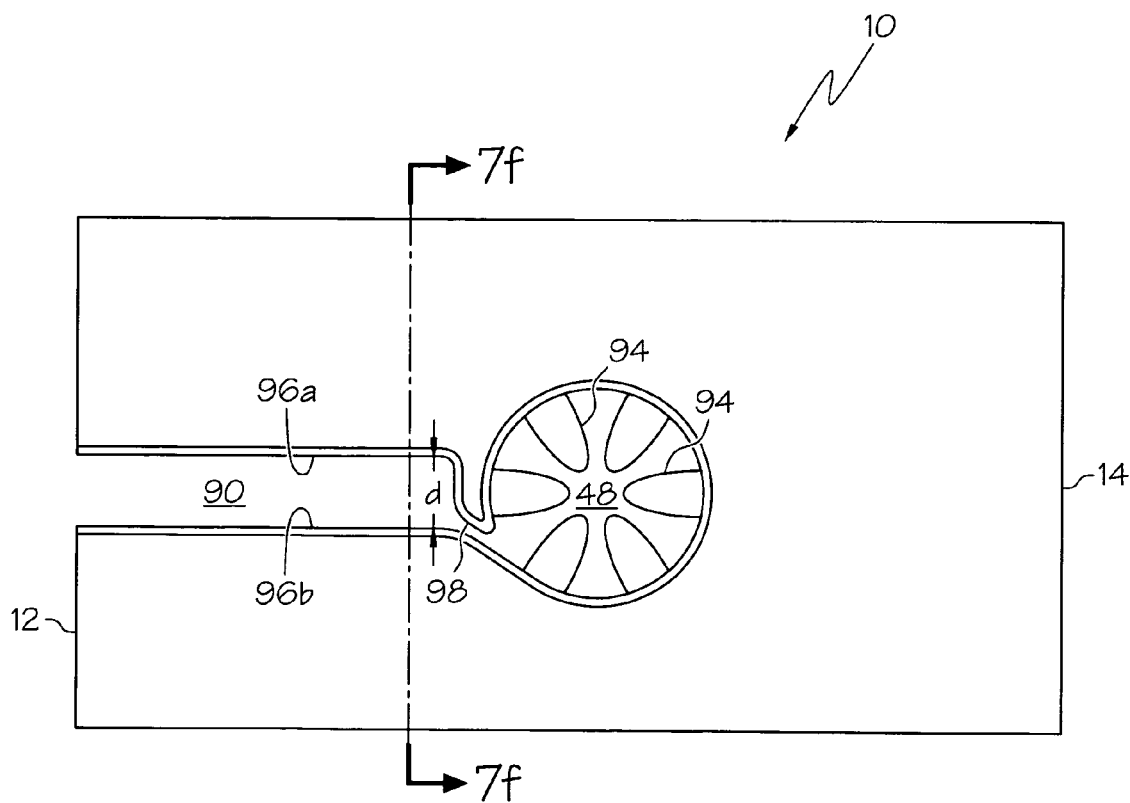
FIG. 7e is a flat view of a stent for a bifurcation where the stent has a slit and a side branch with a finger and petals.

As discussed above, in at least one embodiment, the stent 40 is a substantially cylindrical tubular body with a slit opening, as illustrated in FIGS. 7a, 7c and 7e. In one embodiment, the stent 40 with a slit opening is a self-expanding stent. In one embodiment, the stent 40 with a slit opening is a balloon expandable stent.

The opening has a proximal end 12, a slit region 90 and a distal region 92. In at least one embodiment, at least one band defines the opening by extending about the perimeter of the opening, except for the proximal end 12 which remains open. In FIG. 7c, one continuous band defines the opening. However, it is within the scope of the invention for there to be a plurality of non-continuous bands defining the opening. Thus, there can be one, two, three, four, five, six, seven, eight, nine, ten, or more bands defining the opening.

The proximal end 12 of the stent 40 is the proximal 12 end of the opening. The slit region 90 extends from the proximal end 12 to the distal region 92 of the opening. The longitudinal length of the slit region 90 depends upon the longitudinal location of the distal region 92 along the longitudinal length of the stent 40. Thus, the longitudinal length of the slit region 90 increases the further away the distal region 92 is from the proximal end 12 of the stent 40. The slit region 90 also has a circumferential length (d) which is the distance/length between the edges 96a,b of the slit region. The circumferential length (d) depends upon the size of the guide wire used as well as the design of the stent. In at least one embodiment, the circumferential length (d) between the edges 96a,b is between 0.0 inches and 0.017 inches, or 0.0 mm and 0.4318 mm. In at least one embodiment the circumferential length (d) is between 0.0 inches and 0.038 inches, or 0.0 mm and 0.9652 mm. In at least one embodiment, the circumferential length (d) is between 0.0 mm and 2 mm. In at least one embodiment, the circumferential length (d) between the edges 96a,b tapers. In one embodiment, the circumferential length at the distal end of the slit region is greater than at the proximal end of the slit region 90 and tapers therebetween. In at least one embodiment, the circumferential length (d) between the edges 96a,b varies from the proximal end of the slit region 90 to the distal end of the slit region 90, such as would occur, for example, if the edges 96a,b zig-zag about the circumference of the stent. This embodiment would be an example of the stent design affecting the circumferential length (d) of the slit region 90. In at least one embodiment, the slit region 90 has a smaller circumferential length (d) than the side hole 48. In at least one embodiment, the slit region 90 has the same circumferential length (d) as the side hole 48. In at least one embodiment, the slit region 90 extends parallel to the longitudinal axis of the stent 40, indicated by an arrow.

In at least one embodiment, the edges 96a,b of the slit region 90 are rolled, as shown in FIG. 7d is an end view of this embodiment. Note that although the stent is comprised of a plurality of struts, the drawing depicts the end of the stent as a band of metal so that the structure of the stent can be clearly depicted. In this embodiment, the alignment guide wire 64 goes between the rolled edges 96a,b which subsequently unroll to form a substantially cylindrical tubular body with the alignment guide wire 64 positioned within the lumen of the stent 40. In at least one embodiment, the edges 96a,b of the slit region 90 overlap when unrolled. In at least one embodiment, there is a gap between the edges 96a,b of the slit region 90 when they are in an unrolled state. In at least one embodiment, the gap between the edges 96a,b of the slit region 90 when they are in an unrolled state is substantially zero.

The distal region 92 of the opening is the side hole 48. In at least one embodiment, the side hole 48 has at least one projection 94, as illustrated in FIGS. 7a, 7c and 7e. Thus, it is within the scope of the invention for the side hole 48 to have one, two, three, four, five, six, seven, eight, nine, ten or more projections 94. The at least one projection 94 has an expanded state wherein the at least one projection 94 extends into the branch vessel 22 thereby forming a side branch of the stent 40. The side branch has a lumen that is in communication with the lumen of the substantially cylindrical tubular body of the stent 40. In at least one embodiment, the side hole 48 does not have a projection 94.

In FIG. 7e, the side hole 48 of the stent 10 has a finger 98, which has a projection 94 extending therefrom. Note that since the stent 10 can have any design, the stent 10 in FIG. 7e is shown in flat view without a pattern given for the body of the stent 10 and a band extends about the entire perimeter of the opening. As discussed above, the perimeter of the opening can be defined by a plurality of bands. The finger 98 has a length so that it extends across the slit region 90. In at least one embodiment, the length of the finger 98 is at a minimum equal to ½(d), where d is the circumferential length between the edges 96a,b of the slit region 90 at the junction of the slit region 90 and the side hole 48, as shown in FIG. 7e. In at least one embodiment, the length of the finger 98 is greater than the circumferential length (d) so that when the stent 10 is in an unexpanded state the second edge 96b of the opening overlaps the end of the finger 98. Thus, the finger 98 can have any length so long as it can assume a folded state while the stent 10 is being positioned, an unexpanded state when the alignment guide wire 64 is withdrawn and an expanded state to form a portion of the side branch.

Figure 7F:
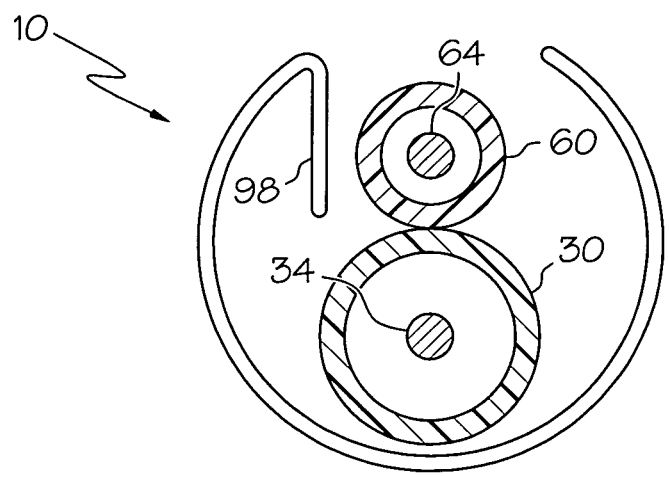
FIG. 7f is an end view of the stent in FIG. 7e taken at line 7f-7f, where the stent is in an unexpanded state and the alignment apparatus of FIG. 1b.

When the stent 10 is in an unexpanded state, e.g. during delivery of the stent to the desired location, the finger 98 with its projection 94 is in a folded state, i.e. folded inwards, so that the alignment guide wire 64 with its alignment sheath 60 is able to position the stent 10 at a bifurcation, as illustrated in FIG. 7f. Once the alignment guide wire 64 has placed the stent 10 in the proper position at a bifurcation, the alignment guide wire 64 is withdrawn proximally so that the alignment guide wire 64 is not extending through the side hole 48 of the stent into the side branch. Once the alignment guide wire 64 is withdrawn, the finger 98 with its projection 94 assumes an unexpanded state where the finger 98 extends towards the opposite side of the side hole 48. When the stent 10 is in an expanded state, the projections 94, including the projection 94 extending from the finger 98, are expanded outward from the body of the stent 10 to form the side branch. Thus, the projection 94 on the finger 98 allows the side branch of the stent 10 to support all around the entire side branch vessel instead of a portion of the side branch vessel circumference.

When the stent 40 with a slit opening (rolled or unrolled) is used with the alignment apparatus 10 of FIG. 1c, the alignment guide wire 64 can remain within the branch vessel 22 and maintain the proper position of the alignment apparatus 10 while the sheaths 30,60 are being withdrawn and the stent 40 deployed, as illustrated in FIG. 7b. FIG. 7b shows the deployment of the stent 40 after the steps illustrated in FIGS. 5a-c. The alignment guide wire 64 does not have to be withdrawn because when the stent 40 is expanded, the alignment guide wire 64 will not be trapped between the stent 40 and the vessel wall because it goes through the slit region 90 into the lumen of the stent 40 as the stent 40 expands and engages the vessel wall.

As discussed above, in at least one embodiment, a dual stent 40 is used at the bifurcation. The dual stent 40 is comprised of a first stent 40a and a second stent 40b. In one embodiment, the dual stent 40 is a self-expanding stent 40. In one embodiment, the dual stent 40 is a balloon expandable stent 40. In one embodiment, the first stent 40a is self-expanding and the second stent 40b is balloon expandable. To differentiate between the first stent 40a and the second stent 40b in FIG. 8c, the crossed lines representing the stent pattern have different orientations. It is within the scope of the invention for the struts forming the first stent 40a and the struts forming the second stent 40b to form the same pattern or different patterns. Thus, first stent 40a and the second stent 40b may have the same strut pattern or different strut patterns.

Both the first stent 40a and the second stent 40b have a proximal end region 12 and a distal end region 14. The struts forming distal end regions 14 of the first and second stents 40a,b extend about the entire circumference of the stent 40a,b, as illustrated in FIGS. 8a and 8b. The distal end region 14 of the second stent 40b is at an oblique angle to the longitudinal axis of the first stent 40a. As used herein, an oblique angle is any angle between 0-90 degrees and includes 90 degrees. In contrast, the struts forming the proximal end regions 12 of the first and second stents 40a,b extend about only a portion of the circumference of the stent 40a,b. In at least one embodiment, the edges of the proximal end regions 12 of the first and second stents 40a,b are complementary so that when they are aligned together a substantially tubular body is formed at the proximal end region 12 when the stents 40a,b are in an expanded state. In at least one embodiment, the complementary edges of the proximal end regions 12 of the first and second stents 40a,b overlap one another. In at least one embodiment, there is a gap between the complementary edges of the proximal end regions 12 of the first and second stents 40a,b.

Figure 6A:
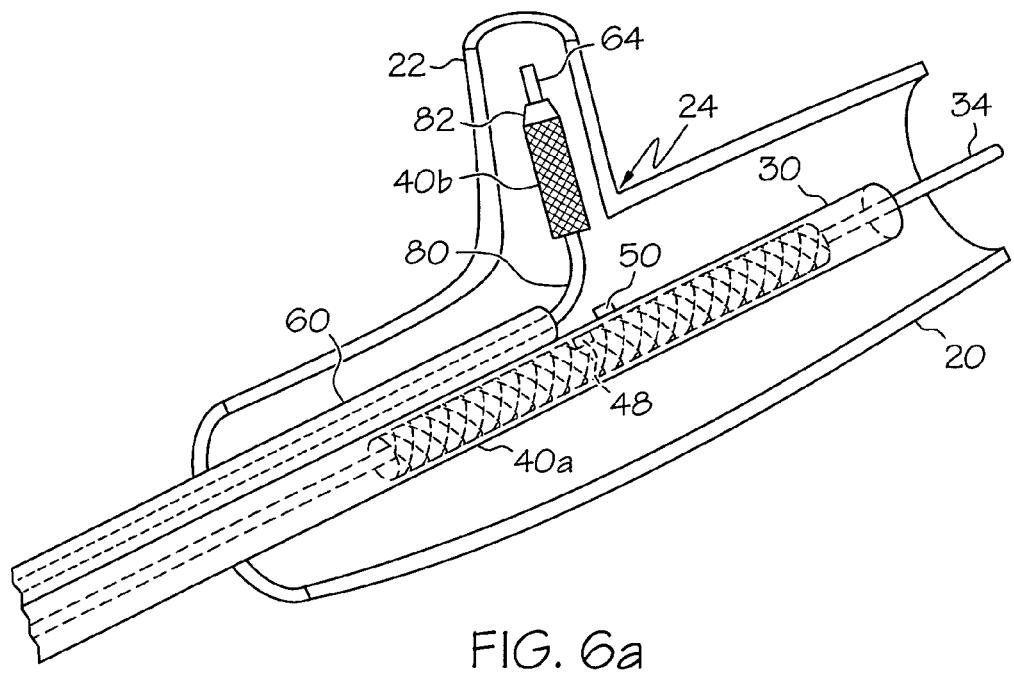
FIG. 6a is a view of an alignment apparatus with a secondary stent on a catheter positioned within the alignment sheath, where the catheter with the secondary stent is advanced along the alignment guide wire out of the alignment sheath into the branch vessel.
Figure 6B:
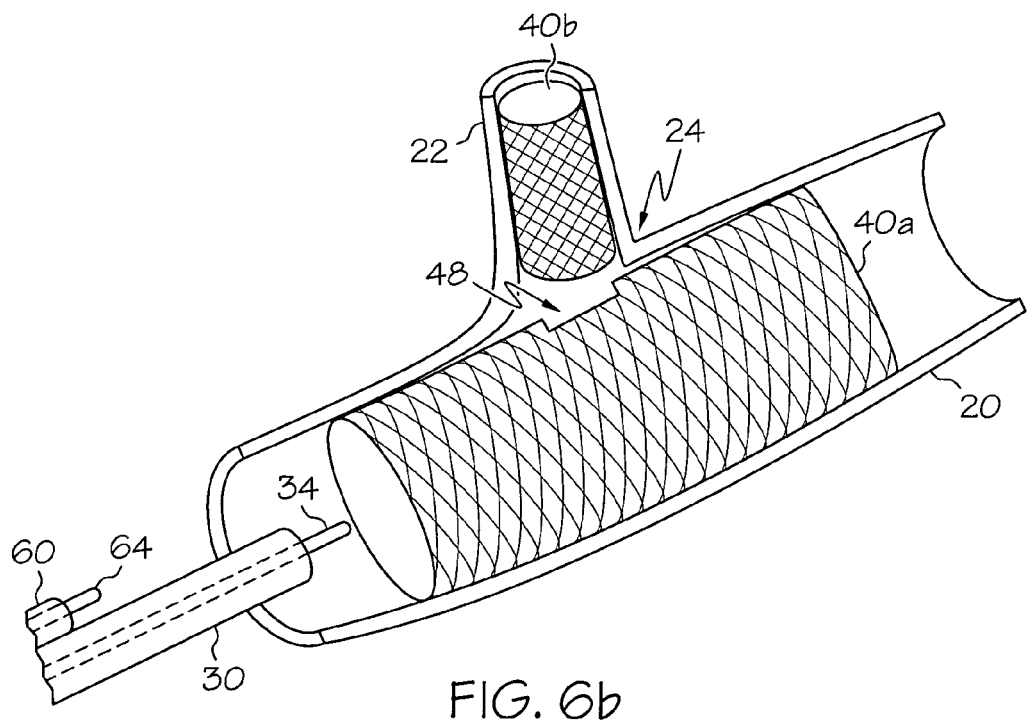
FIG. 6b is a view of the deployed stents after the alignment apparatus has been withdrawn.

Similar to the stent 40 with the slit opening, when the dual stent 40 is used with the alignment apparatus 10 of FIG. 1c, the alignment guide wire 64 can remain within the branch vessel 22 and maintain the proper position of the alignment apparatus 10 while the sheaths 30,60 are being withdrawn and the first stent 40a deployed. The alignment guide wire 64 does not have to be withdrawn because when the first stent 40a is expanded, the alignment guide wire 64 will not be trapped between the first stent 40a and the vessel wall because the proximal end region of the first stent 40a does not form a substantially cylindrical tubular body. After the first stent 40a is deployed, the second stent 40b can be advanced along the alignment guide wire 64 to the proper position at the bifurcation 24 and expanded so that the dual stent 40 is formed at the bifurcation 24, as illustrated in FIG. 8c. It is also within the scope of the invention for the second stent 40b to be expanded first and then the first stent 40a expanded, similar to what is shown in FIGS. 6a and 6b.

The steps to place the stent 40/alignment apparatus 10 combination illustrated in FIG. 4a are the same as discussed above with a few exceptions. Placing the alignment apparatus 10 within the main vessel 20 is done as described above. Once the alignment apparatus 10 is in the proper longitudinal position within the main vessel 20, the alignment apparatus 10 is placed in the proper axial position when the alignment guide wire 34 is advanced through the stent 40, out the side hole 48, through the hole 52 in the exterior sheath 70 and into the branch vessel 22. This places the alignment apparatus 10 in the proper axial orientation relative to the ostium of the branch vessel 22. Then, the alignment guide wire 64 is retracted from the branch vessel 22 back into the alignment sheath 60 so that the exterior sheath 70 can be withdrawn to allow the self-expanding stent to deploy. In at least one embodiment, the stent 40 maintains its axial orientation while the alignment guide wire 64 and the external sheath 70 are withdrawn. Once the stent 40 is deployed within the vessel, the alignment apparatus 10 can be withdrawn from the body or catheters with additional stents 40 can be advanced along the guide wires 34 and 64 to be placed at additional locations.

As shown in FIG. 2d, a secondary stent 40b may be engaged to a catheter 80 positioned within the alignment sheath 60. This embodiment of the alignment apparatus 10 can be advanced to the desired site within the vasculature in the same manner as shown in FIGS. 5a and 5b. The next step is to advance the catheter 80 with the secondary stent 40b along the alignment guide wire 64 into the branch vessel 22, as shown in FIG. 6a. When the secondary stent 40b is in the desired location within the branch vessel 22, the stent 40b can be deployed. Then the main vessel stent 40a can be deployed as shown in FIGS. 5c-5d. FIG. 6b shows how the two stents 40a and 40b would look after being deployed in the vessels. As will be recognized by those skilled in the art, if the side branch requires more than one stent, the stent further away from the main vessel can be deployed into the branch vessel and then a second catheter with a stent engaged thereon can be advanced along the alignment guide wire to the branch vessel, proximal to the first deployed stent.

The sheaths 30,60,70 may be constructed using extrusion, lamination, winding, braiding, molding or bonding. In FIGS. 1a-f, the central sheath 30, the alignment sheath 60 and the external sheath 70 are shown as being made of either the same material or different materials. In at least one embodiment, the central sheath 30, the alignment sheath 60 and the external sheath 70 are manufactured of the same material. In at least one embodiment, the central sheath 30 and the alignment sheath 60 are manufactured of one material while the external sheath 70 is manufactured of a different material. In at least one embodiment, the central sheath 30, the alignment sheath 60 and the exterior sheath 70 each are manufactured from different materials. In at least one embodiment, the central sheath 30 and the alignment sheath 60 are made from different materials. In at least one embodiment, the central sheath 30 and the alignment sheath 60 are made from the same material.

Materials that can be used to manufacture the central sheath 30, the alignment sheath 60, and the external sheath 70, include, but are not limited to, hydrophilic polyurethanes, aromatic polyurethanes, polycarbonate base aliphatic polyurethanes, engineering polyurethane, elastomeric polyamides, block polyamide ethers, polyether block amid (PEBA), silicones, polyether-ester, polyester or linear low density polyethylene, nylon, polyethylene terephthalate (PEI), polybutylene terephthalate (PBT), plastic, stainless steel or nitinol.

In at least one embodiment, at least one of the central sheath 30, the alignment sheath 60 or the external sheath 70 is constructed of layers of material, for example a first layer made of a first material and a second layer made of a second material. In at least one embodiment, at least one sheath 30,60,70 is constructed of a matrix of first material and one or more supportive stripes, strands, members or areas of a second material that is within, external to, or internal to, the matrix of first material. Materials that can be used to manufacture the supportive stripes, strands, members or areas include, but are not limited to, polyamides, polyethylene (PE), Marlex high-density polyethylene, polyetheretherketone (PEEK), polyaryletherketones (PAEK), polyamide (PI), polyetherimide (PEI), polyphenylene oxide (PPO), liquid crystal polymers (LCP), acetal, HDPE, stainless steel and any mixture or combination thereof.

In at least one embodiment, the inner surface of at least one of the central sheath 30, alignment sheath 60 or external sheath 70 has a coating of one or more low friction materials. In at least one embodiment at least one of the central sheath 30, alignment sheath 60 or external sheath 70 includes one or more low friction materials in its construction. Examples of low friction materials include but are not limited to, hydrogel, silicone and Bioslide.

The stents 40 used with the inventive alignment apparatus may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The stents 40 used with the inventive alignment apparatus may be made of shape memory materials such as superelastic Nitinol or spring steel, or may be made of materials which are plastically deformable. In the case of shape memory materials, the stent 40 may be provided with a memorized shape and then deformed to a reduced diameter shape. The stent 40 may restore itself to its memorized shape upon being heated to a transition temperature and having any restraints removed therefrom.

The stents 40 used with the inventive alignment apparatus may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents 40 disclosed herein.

In some embodiments the at least a portion of the stent 40 or the alignment apparatus 10 is configured to include one or more mechanisms for the delivery of a therapeutic agent. Often the agent will be in the form of a coating or other layer (or layers) of material placed on a surface region of the stent 40, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The following numbered statements characterize methods of using an alignment apparatus:

1. A method of placing an alignment apparatus in the proper longitudinal and axial position relative to a desired side branch at a vessel bifurcation comprising:
   providing an alignment apparatus, the alignment apparatus comprising a central sheath, an alignment sheath, and a first stent, the central sheath and the alignment sheath each having a wall and a distal end, the wall of the alignment sheath engaged to the wall of the central sheath, the wall of the central sheath defining a central lumen, a central guide wire extending within the central lumen, the wall of the alignment sheath defining an alignment lumen, an alignment guide wire extending within the alignment lumen, the distal end of the alignment sheath positioned proximally to the distal end of the central sheath, the first stent disposed about one of the alignment guide wire or the central guide wire, the first stent having a pre-delivered state, the first stent in the pre-delivered state contained within at least one of the central sheath and the alignment sheath, the alignment apparatus having a marker, the maker capable of being visualized by an imaging device;
   introducing the alignment apparatus into a body lumen;
   visualizing the alignment apparatus by the imaging device;
   advancing the alignment apparatus through the body lumen until the marker of the alignment apparatus is visualized next to the desired side branch, thereby placing the alignment apparatus into the proper longitudinal position;
   advancing the alignment guide wire into the desired side branch, thereby axially rotating the alignment apparatus into the proper axial orientation.

2. The method of statement 1, the first stent a self-expanding stent, the first self-expanding stent disposed about the central guide wire and contained within the central sheath and further comprising the step of withdrawing both the alignment sheath and the central sheath, thereby deploying the first self-expanding stent into the body lumen.

3. The method of statement 2, the first stent comprising a substantially cylindrical tubular body, the tubular body having a proximal end and defining a primary lumen, the tubular body comprising a wall and at least one perimeter member defining at least one opening in the wall, the at least one opening having a proximal end, a slit region and a distal end region, the proximal end of the opening being the proximal end of the substantially cylindrical tubular body, the slit region extending from the proximal end of the substantially cylindrical tubular body to the distal end region of the at least one opening, the distal end region of the at least one opening an expandable side branch having an expanded state, in the expanded state the at least one expandable side branch defining a side branch lumen, the side branch lumen being in fluid communication with the primary lumen.

4. The method of statement 2, further comprising a first balloon catheter and a second stent, the first balloon catheter disposed about the alignment guide wire, the second stent a balloon expandable stent, the first and second stents each having a proximal end region and a distal end region, the first stent having a longitudinal axis, the distal end regions forming a substantially cylindrical tubular body, the distal end region of the second stent at an oblique angle to the longitudinal axis of the first stent, the proximal end region of the first stent having a first edge, the proximal end region of the second stent having a second edge, the first edge and the second edge complementary to one another and further comprising the step of advancing the first balloon catheter into the side branch, and expanding the balloon thereby expanding and deploying the second stent.

5. The method of statement 1, the alignment apparatus further comprising an external sheath, the first stent a self expanding stent, the first self expanding stent disposed about the alignment sheath and the central sheath and contained within the external sheath and further comprising the step of withdrawing the external sheath thereby deploying the first self-expanding stent.

6. The method of statement 1, the alignment apparatus further comprising a first catheter, the first catheter disposed about the central guide wire, the first stent engaged to the first catheter, the first stent a balloon expandable stent, and further comprising the steps of:

withdrawing both the alignment sheath and the central sheath; and expanding the balloon thereby expanding and deploying the first stent.

7. The method of statement 1, the alignment apparatus further comprising a first catheter, a second catheter, a first stent and a second stent, the first catheter disposed about the central guide wire, the first stent engaged to the first catheter, the first stent a balloon expandable stent, the second catheter disposed about the alignment guide wire, the second stent a balloon expandable stent, the second stent engaged to the second catheter and further comprising the steps of advancing the second catheter along the alignment guide wire into the desired side branch;

expanding the balloon thereby expanding and deploying the second stent;

withdrawing both the alignment sheath and the central sheath; and expanding the balloon thereby expanding and deploying the first stent.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. An alignment apparatus, the alignment apparatus comprising a central sheath, an alignment sheath, and a first stent, the central sheath and the alignment sheath each having a wall and a distal end, the wall of at least the distal end of the alignment sheath engaged to the wall of the central sheath so that the distal end of the alignment sheath has a fixed position relative to the central sheath, the wall of the central sheath defining a central lumen, a central guide wire extending within the central lumen, the wall of the alignment sheath defining an alignment lumen, an alignment guide wire extending within the alignment lumen, the distal end of the alignment sheath positioned proximally to the distal end of the central sheath, the first stent disposed about one of the alignment guide wire or the central guide wire, the first stent having a pre-delivered state, the first stent in the pre-delivered state contained within at least one of the central sheath and the alignment sheath.

2. The alignment apparatus of claim 1, the wall of the central sheath forming a portion of the wall of the alignment sheath.

3. The alignment apparatus of claim 2, further comprising an exterior sheath, the exterior sheath disposed about both the central sheath and the alignment sheath.

4. The alignment apparatus of claim 1, the alignment apparatus having at least one marker, the maker capable of being visualized by an imaging device.

5. The alignment apparatus of claim 4, the at least one marker engaged to the wall of the central sheath.

6. The alignment apparatus of claim 1, further comprising a first catheter, the first catheter disposed about the central guide wire, the first stent engaged to the first catheter.

7. The alignment apparatus of claim 6, further comprising a second catheter and a second stent, the second catheter disposed about the alignment guide wire, the second stent engaged to the second catheter.

8. The alignment apparatus of claim 1, the first stent comprising a substantially cylindrical tubular body, the tubular body having a proximal end and defining a primary lumen, the tubular body comprising a wall and at least one perimeter member defining at least one opening in the wall, the at least one opening having a proximal end, a slit region and a distal end region, the proximal end of the opening being the proximal end of the substantially cylindrical tubular body, the slit region extending from the proximal end of the substantially cylindrical tubular body to the distal end region of the at least one opening.

9. The alignment apparatus of claim 8, the slit region having a first edge and a second edge, in the pre-delivered state the first and second edges are rolled, in the delivered state the first and second edges are unrolled.

10. The alignment apparatus of claim 1, further comprising a second stent, the first stent disposed about the central guide wire and having a longitudinal axis, the second stent disposed about the alignment guide wire, the first and second stents each having a proximal end region and a distal end region, the distal end regions of the first and second stents each forming a substantially cylindrical tubular body, the distal end region of the second stent having a longitudinal axis at an oblique angle to the longitudinal axis of the first stent, the proximal end region of the first stent having a first edge, the proximal end region of the second stent having a second edge, the first edge complementary to the second edge.

11. The alignment apparatus of claim 1, wherein the wall of the alignment sheath and the wall of the central sheath are engaged by bonding, welding, or adhesive.

12. An alignment apparatus, the alignment apparatus comprising a central sheath, an alignment sheath, and a stent, the central sheath and the alignment sheath each having a wall and a distal end, the wall of at least the distal end of the alignment sheath engaged to the wall of the central sheath so that the distal end of the alignment sheath has a fixed position relative to the central sheath, the wall of the central sheath defining a central lumen, a central guide wire extending within the central lumen, the wall of the alignment sheath defining an alignment lumen, an alignment guide wire extending within the alignment lumen, the distal end of the alignment sheath positioned proximally to the distal end of the central sheath, the stent having a first portion and a second portion, the first portion disposed about at least a portion of the alignment sheath, the second portion disposed about at least a portion of the central sheath.

13. The alignment apparatus of claim 12, the wall of the central sheath forming a portion of the wall of the alignment sheath.

14. The alignment apparatus of claim 12, the alignment apparatus having at least one marker, the marker capable of being visualized by an imaging device.

15. The alignment apparatus of claim 12, further comprising an external sheath, the external sheath disposed about the stent.

16. The alignment apparatus of claim 12, the stent comprising a substantially cylindrical tubular body, the tubular body having a proximal end and defining a primary lumen, the tubular body comprising a wall and at least one perimeter member defining at least one opening in the wall, the at least one opening having a proximal end, a slit region and a distal end region, the proximal end of the opening being the proximal end of the substantially cylindrical tubular body, the slit region extending from the proximal end of the substantially cylindrical tubular body to the distal end region of the at least one opening.

17. The alignment apparatus of claim 16, the distal end region of the at least one opening an expandable side branch, the expandable side branch in an expanded state defining a side branch lumen, the side branch lumen being in fluid communication with the primary lumen.

18. The alignment apparatus of claim 16, the stent having a pre-delivered state and a delivered state, the slit region having a first edge and a second edge, in the pre-delivered state the first and second edges are rolled, in the delivered state the first and second edges are unrolled.

19. The alignment apparatus of claim 12, wherein the wall of the alignment sheath and the wall of the central sheath are engaged by bonding, welding, or adhesive.

* * * * *